United States Patent [19]

Williams

[11] Patent Number: 4,628,930

[45] Date of Patent: Dec. 16, 1986

[54] SOOTHING COMFORT GIRDLE

[76] Inventor: Steven N. Williams, 1520 Dewberry #107, Lancaster, Tex. 75146

[21] Appl. No.: 790,936

[22] Filed: Oct. 24, 1985

[51] Int. Cl.$^4$ .............................. A61F 7/00; H05B 3/36
[52] U.S. Cl. ......................................... 128/379; 2/406; 128/402; 219/211; 219/527
[58] Field of Search ............... 128/379, 384, 385, 386, 128/387, 399, 402; 2/406; 219/211, 212, 527, 528, 529

[56] References Cited

U.S. PATENT DOCUMENTS

| | | |
|---|---|---|
| D. 99,529 | 5/1936 | Spanel . |
| D. 134,791 | 1/1943 | Selver . |
| D. 258,770 | 4/1981 | Stern . |
| 2,497,443 | 2/1950 | Eatman ............................ 128/402 |
| 2,590,212 | 3/1952 | Samuels ......................... 128/387 X |
| 3,396,264 | 8/1968 | Murphy et al. ................. 128/382 X |
| 3,500,014 | 3/1970 | Longo . |
| 3,501,616 | 3/1970 | Arron ............................. 128/402 X |
| 3,518,995 | 7/1970 | Claff ................................. 128/379 |
| 3,680,563 | 8/1972 | Forrest ............................. 128/402 |
| 3,797,501 | 3/1974 | Di Tullio . |

*Primary Examiner*—Anton O. Oechsle
*Attorney, Agent, or Firm*—Henderson & Sturm

[57] ABSTRACT

A girdle for use in preventing the discomfort of cramps due to a menstrual period. The girdle has a cotton cloth panty of a type having a front portion, a rear portion and interconnecting side portions. The panty has a continuous elastic material around the top thereof and has a battery holding compartment attached to the top to a central front portion thereof. An electrical resistance heating structure is attached to the outside of the cotton panty front portion and extends from the crotch portion thereof an upwardly and outwardly in a V-shaped configuration to where the battery holding compartment is attached to the elastic. An electric battery is removably disposed of the battery holding compartment. A V-shaped basket weave cloth structure having a higher R-value than that of the cotton cloth of which the front portion is constructed is disposed over the front of the electrical heating structure for causing heat from the electrical heating structure to tend to flow through the cotton front panel towards the person wearing the girdle rather than through the front basket weave cloth whereby such person wearing the girdle will have that part of her anatomy which tends to cramp during menstrual periods heated during a menstrual period.

4 Claims, 5 Drawing Figures

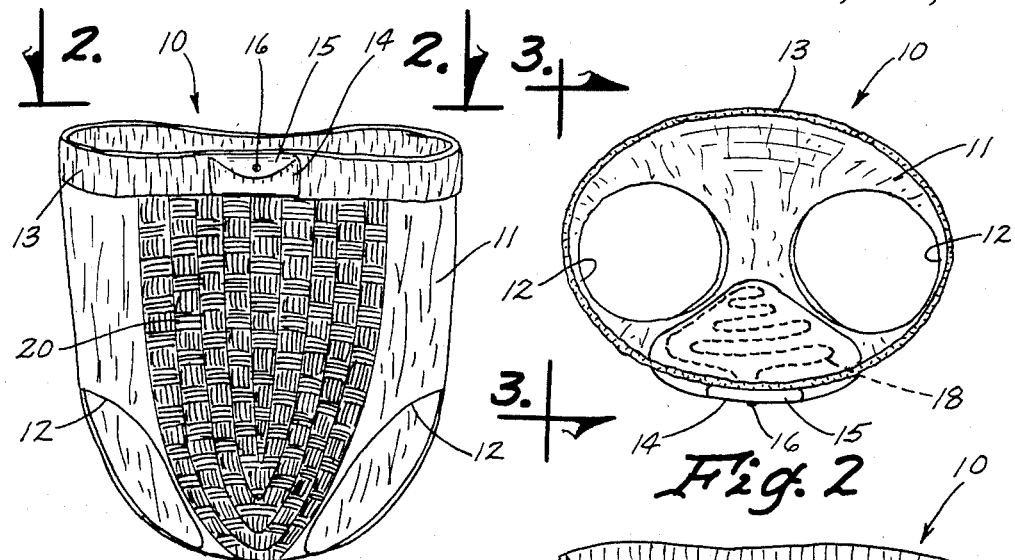
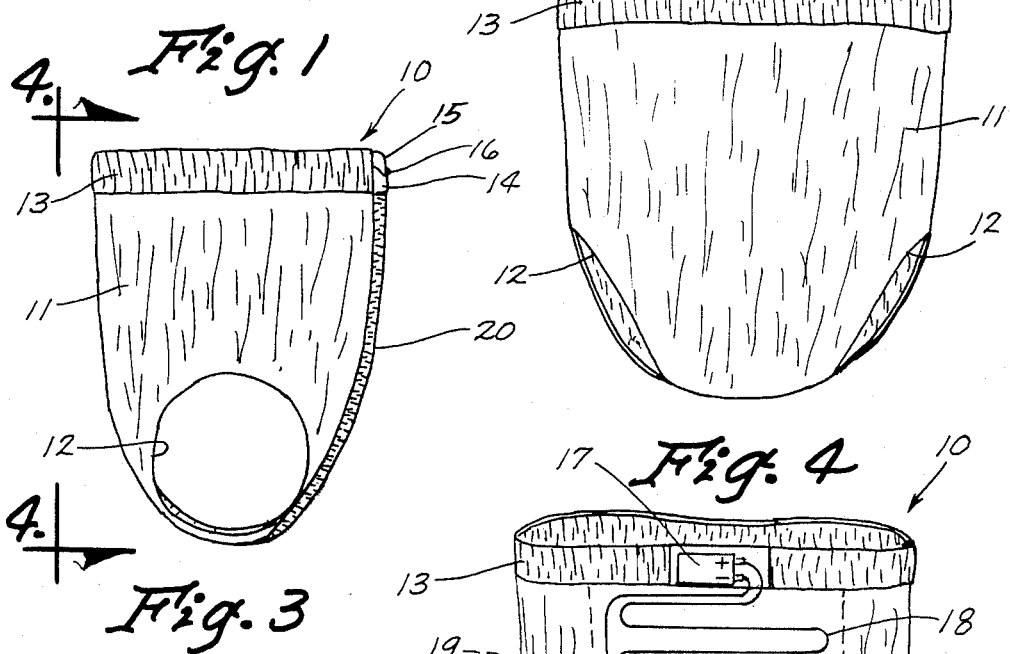
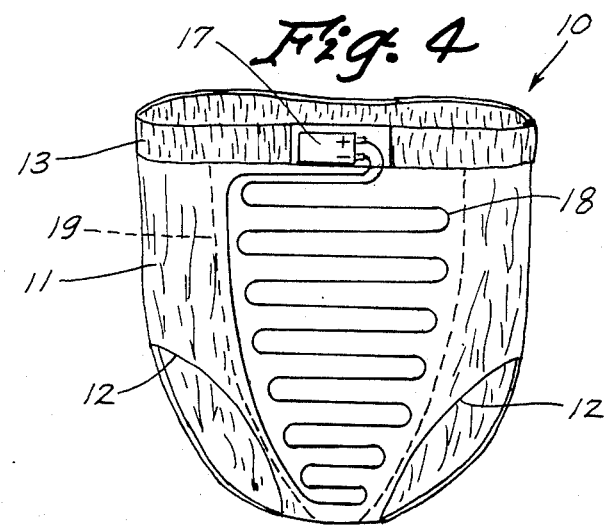

SOOTHING COMFORT GIRDLE

TECHNICAL FIELD

The present invention relates to a girdle and more particularly to a girdle having an electrical thermal pad installed therein for preventing cramps in women during their menstrual period.

BACKGROUND ART

Most women experience cramps during their menstrual cycle. The cramps occur in the lower abdominal area corresponding to the front and lower crotch portion of a girdle or undergarment. The reason for these cramps is due to blood loss to this region, thereby causing muscular contraction in the body's attempt to create heat. This is similar to the reason why a person shivers when cold. A common solution to the problem is to take one or more of the many drugs or medicines that have been developed for this purpose. Not only do these drugs merely mask the pain, but quite often they are not effective to accomplish this purpose. Often times these drugs have serious side effects. Consequently, there is a need for some way to prevent cramps during menstrual period to reduce the pain in a safe and economical way.

DISCLOSURE OF THE INVENTION

The present invention relates to a girdle for use in preventing the discomfort of cramps due to a menstrual period. The girdle has a cotton cloth panty of a type having a front portion, a rear portion and interconnecting side portions. The panty has a continuous elastic material around the top thereof and has a battery holding compartment attached to the top to a central front portion thereof. An electrical resistance heating structure is attached to the outside of the cotton panty front portion and extends from the crotch portion thereof an upwardly and outwardly in a V-shaped configuration to where the battery holding compartment is attached to the elastic. An electric battery is removably disposed of the battery holding compartment. A V-shaped basket weave cloth structure having a higher R-value than that of the cotton cloth of which the front portion is constructed is disposed over the front of the electrical heating structure for causing heat from the electrical heating structure to tend to flow through the cotton front panel towards the person wearing the girdle rather than through the front basket weave cloth whereby such person wearing the girdle will have that part of her anatomy which tends to cramp during menstrual periods heated during a menstrual period.

An object of the present invention is to provide a way to prevent cramps during the menstrual period.

Another object of the invention is to prevent the pain associated with cramps in the menstrual period without the use of drugs or medicines.

A further object of the present invention is to heat the abdominal region of the body and help to keep it at a constant temperature to prevent cramps during a menstrual period.

Other objects, advantages, and novel features of the present invention will become apparent from the following detailed description of the invention when considered in conjunction with the accompanying drawings.

BRIEF DESCRIPTION OF THE DRAWINGS

FIG. 1 is a front elevational view of a girdle constructed in accordance with the present invention;

FIG. 2 is a top view taken along line 2—2 of FIG. 1 and showing electrical system wires in dashed lines;

FIG. 3 is a side elevational view taken along line 3—3 of FIG. 2;

FIG. 4 is a rear view taken along line 4—4 of FIG. 3; and

FIG. 5 is a view like FIG. 1 but showing the basket weave front portion and battery compartment removed therefrom to show the resistance wires hooked to a battery in the elastic portion of the girdle.

BEST MODE FOR CARRYING OUT THE INVENTION

Referring now to the drawings wherein like reference numerals designate identical or corresponding parts throughout the several views, FIG. 1 shows a girdle (10) constructed in accordance with the present invention. The girdle (10) includes a cotton panty having front, rear and side portions (11) constructed of cotton cloth. Openings (12) are disposed in the panty (11) for permitting legs to extend therethrough. An elastic waistband (13) is sewn to the top of the cotton panty portion (11) as can readily be seen in the drawings. A battery compartment (14) is sewn to the elastic portion (13) and has a flap (15) thereon and a snap (16) on the flap (15) for permitting a battery to be received within the pocket (14) and to have ready access thereto for changing such battery when it loses its power.

Referring now to FIG. 5, it is noted that a battery (17) is shown with the battery compartment (14) taken away and electrical resistance wire (18) has the ends thereof electrically connected to the battery (17), such as by snaps which are common place in connecting a 9-volt battery electrically to something which will use the power therefrom. The dashed lines (19) shown in FIG. 5 are present to show the stitching which would be present to connect a basket weave cloth structure (20) to the front portion of the cloth panty (11). Consequently, the electrical resistance wire (18) is sandwiched in between the heavy basket weave portion (20), which can be composed of polyester material or any other material having a higher R-value than that of the cotton cloth (11). The reason for this relationship is so that the heat from the heating element (18) will tend to flow towards the person wearing the girdle (10) rather than to be lost into the atmosphere. Because the heating element (18) is positioned in the region where cramps occur due to heat loss during a menstrual period, the presence of the heat energy will tend to stabilize the temperature and keep such temperature relatively constant, thereby preventing the pain associated with cramps without the use of drugs and medicines.

Consequently it will be appreciated that the preferred embodiment of the present invention as described above does indeed accomplish the aforementioned objects. Obviously many modifications and variations of the present invention are possible in light of the above teachings. It is therefore to be understood that, within the scope of the appended claims, the invention may be practiced otherwise than as specifically described.

I claim:

1. A girdle for use in preventing the discomfort of cramps due to a menstrual period, said girdle comprising:

a cotton cloth panty of a type having a front portion, a rear portion and interconnecting side portions;

means for forming a leg hole in a bottom portion of each side portion thereof;

means attached to the front and rear portions thereof for forming a crotch portion between the leg holes;

continuous elastic means connected to the extreme top portions of said front, rear and side portions for forming an access opening at the top of said girdle;

means for forming a battery holding compartment attached to said elastic means;

electrical heating means attached to the front of said front portion for producing heat to prevent cramps during the menstrual cycle, said electrical heating means extending from said crotch portion to said elastic means;

an electric battery removably disposed in said battery holding compartment means;

means for electrically connecting said battery to said electrical heating means whereby the energy from said battery will generate heat in said electrical heating means;

a generally V-shaped basket weave cloth means having a higher R-value than said cotton cloth of which said front portion is constructed disposed over said electrical heating means for causing most of the heat from said heating means to flow through said cotton front panel rather than through said basket weave cloth whereby a person wearing the girdle will have the part of her anatomy which tends to cramp during menstrual periods heated to prevent such cramps.

2. The girdle of claim 1 wherein said battery holding compartment comprises a pocket attached to a front central part of said elastic means, said pocket including a snap type closure means thereon for selectively holding a battery in said pocket or permitting said battery to be easily replaced.

3. The apparatus of claim 2 wherein said basket weave cloth is made of a synthetic material.

4. The apparatus of claim 3 wherein said basket weave cloth comprises polyester material.

* * * * *